United States Patent
Wang et al.

(10) Patent No.: US 9,253,448 B1
(45) Date of Patent: Feb. 2, 2016

(54) SYSTEM AND METHOD FOR DETERMINATION OF CONTACT LENS ORIENTATION

(75) Inventors: Lei Wang, Wayland, MA (US); Alex Zatsman, Newton, MA (US); Lowell Jacobson, Grafton, MA (US)

(73) Assignee: Cognex Corporation, Natick, MA (US)

( * ) Notice: Subject to any disclaimer, the term of this patent is extended or adjusted under 35 U.S.C. 154(b) by 516 days.

(21) Appl. No.: 13/338,775

(22) Filed: Dec. 28, 2011

(51) Int. Cl.
*H04N 7/18* (2006.01)
*G01N 21/90* (2006.01)

(52) U.S. Cl.
CPC .............. *H04N 7/18* (2013.01); *G01N 21/90* (2013.01); *G01N 21/9027* (2013.01)

(58) Field of Classification Search
CPC ............ G01M 11/00278; G06Q 30/02; G08B 13/19619
USPC ............ 348/92, 125, 127, 130, 143; 382/141, 382/190, 224
See application file for complete search history.

(56) References Cited

U.S. PATENT DOCUMENTS

| | | | |
|---|---|---|---|
| 5,500,732 A | 3/1996 | Ebel et al. | |
| 6,765,661 B2 | 7/2004 | Biel et al. | |
| 6,909,503 B2 | 6/2005 | Baske et al. | |
| 7,256,881 B2 | 8/2007 | Leppard et al. | |
| 7,423,747 B2 | 9/2008 | Biel et al. | |
| 7,663,742 B2 | 2/2010 | Biel et al. | |
| 7,855,782 B2 | 12/2010 | Biel et al. | |
| 7,990,531 B2 | 8/2011 | Clements et al. | |
| 8,340,364 B2 * | 12/2012 | Tosa | 382/117 |
| 2009/0303465 A1 * | 12/2009 | Clements et al. | 356/124 |
| 2010/0220185 A1 * | 9/2010 | Vertoprakhov et al. | 348/92 |

FOREIGN PATENT DOCUMENTS

WO 2007091124 A2 8/2007

* cited by examiner

*Primary Examiner* — Andy Rao

(57) ABSTRACT

This invention provides a system and method to determine orientation/pose of a contact lens residing on the transparent bottom of a fluid-filled, typically opaque-sided cuvette. This allows the system to determine whether the subject contact lens is in a concave up or concave down orientation, and whether the lens is everted. An illuminator is aligned on a longitudinal axis of the cuvette through the contact lens at a position over the cuvette, and a vision system camera is aligned beneath the bottom of the cuvette on the axis. In alternate embodiments the axial locations of the camera and the illuminator can be varied. The camera acquires images of the contact lens. The vision system associated finds the appropriate contact lens edges and characteristics of features. These features allow each of the four poses to be distinguished and categorized for either an acceptable/good or unacceptable/bad pose within the cuvette.

18 Claims, 4 Drawing Sheets

SYSTEM AND METHOD FOR DETERMINATION OF CONTACT LENS ORIENTATION

FIELD OF THE INVENTION

This invention relates to the use of vision systems in testing manufactured products, and more particularly to the testing of contact lenses.

BACKGROUND OF THE INVENTION

The wearing of contact lenses is a popular technique for correcting a variety of vision problems. So-called "soft" contact lenses are particularly popular with wearers because they consist of a high water volume and conform closely to the wearer's eye. This significantly increases the comfort of the wearer, particularly when a contact lens is worn over a long duration.

Like many other medical products, contact lenses are expected to meet high standards for quality and reliability. As part of the quality assurance and quality control (QAQC) procedures in manufacturing contact lenses, specimens from some or all of the manufactured batches are subjected various test processes. This ensures generally that the manufacturing processes are sound and that a stable level of quality is maintained over time. An approach to testing a sample contact lens entails loading it manually or automatically (e.g. robotically) into a fluid-filled (e.g. saline) cuvette, and testing the contact lens. An exemplary cuvette is a glass or polymer tube with a flat transparent bottom. Notably, processes can be properly performed on the subject contact lens if the contact lens rests on the bottom of the cuvette in a concave down orientation, and is not everted (inside out). While the manual or automated loading process makes efforts to ensure the lens is in the desired non-everted, concave-down orientation, there are times when the contact lens is loaded improperly. In fact, there are four possible orientations ("poses") for a soft contact lens resting on the bottom of a fluid-filled cuvette for any given inspection cycle. These four loaded poses are:
1. non-everted concave down (CCD, good)
2. non-everted concave up (CCU, bad)
3. everted concave down (ECCD, bad)
4. everted concave up (ECCU, bad)

If the contact lens has pose 1 (CCD, good), then it can be transferred to one or more further processes. If the contact lens has pose 2 (CCU, bad), it should be flipped into the correct orientation, requiring further physical action before proceeding to further processes. If the contact lens has pose 3 or 4 (ECCD or ECCU, both bad), it is typically discarded, as it has experienced possible plastic deformation that renders it imperfect.

While it may be possible to determine the pose of a contact lens readily based upon a side view image of it in the cuvette, the processes to which the contact lens is subjected employ a cuvette with opaque or diffusive side walls. It is therefore not practical to obtain a side view of the lens. Rather, only a top or bottom view with front or back lighting of the contact lens is attainable, i.e. a "face-on" view. It is more challenging to determine the pose of the contact lens (either manually or using a vision system application) from this view point.

It is therefore desirable to provide a system and method for determining the orientation/pose of a contact lens with respect to a cuvette in a face-on view, using a vision system that can distinguish between various poses based upon such direct, face-on view of the top or bottom surface of the contact lens. This system and method should allow for relatively quick categorization of the pose so that further processes (if desired) can be employed with respect to the contact lens and should enable the use of commercially available illuminators and vision system components.

SUMMARY OF THE INVENTION

This invention overcomes disadvantages of the prior art by providing a system and method that employs vision system tools to determine the orientation or pose of a contact lens residing on the transparent bottom of a fluid-filled, typically opaquesided or diffusive-sided cuvette. This allows the system to determine whether the contact lens is in a concave up or concave down orientation, and whether the lens is everted. In an illustrative embodiment, an illuminator is aligned approximately on a longitudinal axis of the cuvette through the contact lens at a position over the cuvette. A vision system camera is aligned beneath the bottom of the cuvette approximately on the axis to acquire a face-on view of the contact lens. In alternate embodiments the axial locations of the camera and the illuminator can be varied. The camera acquires one or more (typically grayscale) images of the contact lens. The vision system associated with the camera operates vision system tools to find the appropriate contact lens edges and to identify the characteristic features within the perimeter of the lens in the vicinity of the perimeter edge. These features allow each of the four poses to be distinguished and categorized. These vision system tools can determine, illustratively, subtle cues in the acquired image of the contact lens. These cues include focus gradients and dark/bright bands near the edge of the lens. Illustratively, the system and method processes the contact lens image to obtain (a) an average radial intensity profile near the edge of the contact lens and (b) a focus gradient profile measured in the radial direction from the lens center to its edge. These raw profiles (as well as features computed from these profiles) are used to classify the pose of each lens. This classification can be based upon one of a plurality of sets of image features for each pose of lens. These features can be derived from a plurality of acquired images of actual contact lenses in each pose. Typically a large number of training images for each pose can be trained and the classification of the pose of the contact lens in the runtime image is based upon conformity to the training image(s) using vision tool conventional techniques.

In an illustrative embodiment, the system and method can be used to classify the pose of a variety of differing contact lens types. Such types include, but are not limited to, spherical, toric, and those contact lenses with or without printed iris designs (e.g. eye-color-changing contact lenses).

BRIEF DESCRIPTION OF THE DRAWINGS

The invention description below refers to the accompanying drawings, of which.

DETAILED DESCRIPTION

Figure 1:
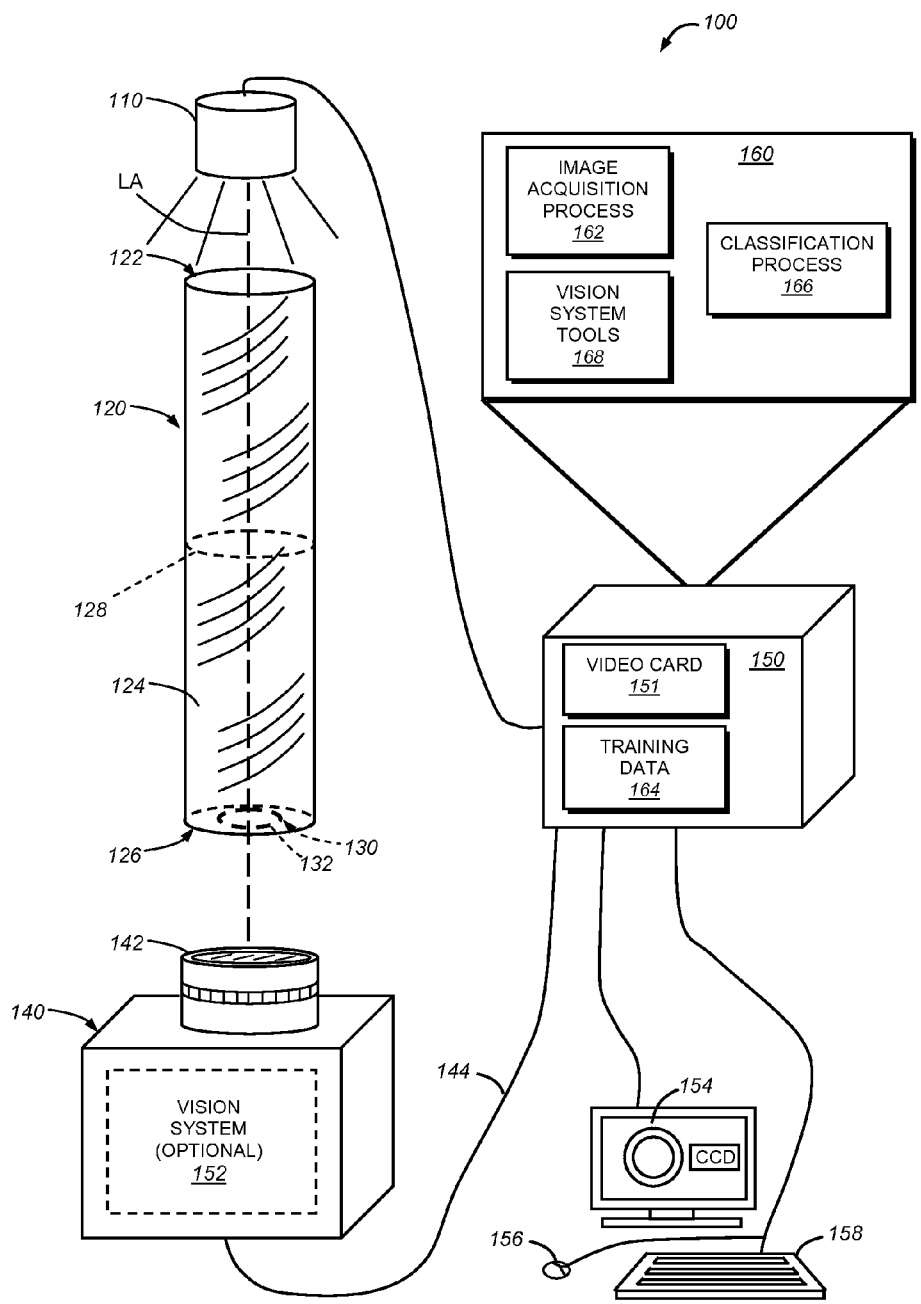
FIG. 1 is a diagram of an arrangement for determining the orientation or pose of a contact lens in a fluid-filled cuvette with a vision system, in which the camera thereof is aligned approximately along a longitudinal axis of the cuvette.

FIG. 1 shows an arrangement 100 for use in performing the classification of contact lens poses prior to further processes either at the same location or a subsequent station (not shown). For clarity, a robotic manipulator that handles contact lenses and the underlying cuvette holder and various supporting structures have been omitted. Such devices and structures can be present and implemented in accordance with either conventional or custom designs.

The arrangement 100 includes an illuminator 110 of any acceptable type, which in this embodiment is aligned to direct light approximately along a longitudinal axis LA of a cuvette 120. As described generally above the cuvette 120 defines a tube that can be circular, square or another cross-sectional shape. The cuvette 120 includes an open top 122 through which the light from the illuminator 110 passes. The sidewall(s) 124 of the cuvette 120 are shaded to indicate a generally opaque or diffuse surface—for example, a matte black surface coating, a frosted/rough surface, or the like. In this manner, light penetrates the cuvette mainly through the top and also, illustratively, through a transparent, enclosed bottom 126. As shown by the dashed fill-line 128, the cuvette 120 is filled with an acceptable fluid such as saline to a level that fully covers an exemplary contact lens 130 resting against the interior side of the cuvette bottom 126. The cuvette 120 can be constructed from glass, crystal, polymer or any other material (or combination of materials) that allows for a clear, light-transmissive, and generally non-distorting bottom 126. The longitudinal (i.e. top-to-bottom) length and cross-sectional dimension (e.g. diameter) of the cuvette is highly variable. The length is sufficient to provide full fluid coverage of the contained contact lens 130. The cross-section of the sidewall(s) is at least large enough to provide clearance for the outer edge 132 of the contact lens 130 and the inside surface of the sidewall 124 can be located a few millimeters radially beyond the outer edge 132 of the contact lens 130. This ensures that the contact lens has sufficient clearance within the cuvette and a good image can be acquired.

The image of the exemplary contact lens 130 is acquired by a vision system camera 140 that can be of conventional design. In an embodiment, the camera 140 includes a lens 142 that is adapted to acquire detailed images of an object the size of a contact lens. The lens optical axis is approximately aligned with the longitudinal axis LA of the cuvette so as to provide a straight-on view of the contact lens 130. An appropriate image sensor (not shown) mounted orthogonally to the optical axis within the camera is used to capture the image and convert it to pixel data, typically in grayscale, but optionally in color. In an illustrative embodiment, the pixel data is transmitted by an appropriate link 144 (wired and/or wireless) to a vision system processor, which can be a standalone computer (e.g. PC 150) with an appropriate video acquisition peripheral 151 (e.g. a framegrabber, etc.). Alternatively, the vision system processor can comprise another type of networked data processing system (not shown), or an on-camera vision system processor 152 (shown in phantom), that carries out appropriate vision system processes and provides inspection results either via an interface and/or using an indicator assembly mounted on the camera body. The illustrative computer 150 contains conventional interface devices, such as a display 154, mouse 156 and keyboard 158. This is exemplary of a variety of interface arrangements (e.g. a touch screen), some of which are purpose-built for the particular vision task. For example, the computer 150 or other processor(s) can interface with a robot controller (not shown) that manipulates contact lenses, contact lens packages, cuvettes and/or other elements of the arrangement.

The vision system processor/process 160 resides within the computer 150 as a software process consisting of a non-transitory computer-readable medium of program instructions. The vision system process and any other processes herein can be implemented alternatively as hardware, or a combination of hardware and software. Note also, the term "process" as used herein should be taken broadly to include hardware and software based process blocks, which can be combined, in whole or in part, with other process blocks. Likewise, a given process or processor can be divided into a plurality of sub-processes or sub-processors as appropriate. The vision system process 160 includes an image acquisition and image data handling process 162 that acquires, transmits and stores image data from the camera 140 with respect to contact lenses (130). The image data is then analyzed, as described below, by one or more vision system tools 168 (which can be conventional in structure and function) to recognize and evaluate certain features in the contact lens image. Based upon the identified features and their particular characteristics, the vision system applies a classification process 166 that can be trained using stored training data 164 based on models of contact lenses in certain poses. This classification process thereby decides which pose (CCD, CCU, ECCD or ECCU, above) the contact lens exhibits.

Figure 2:
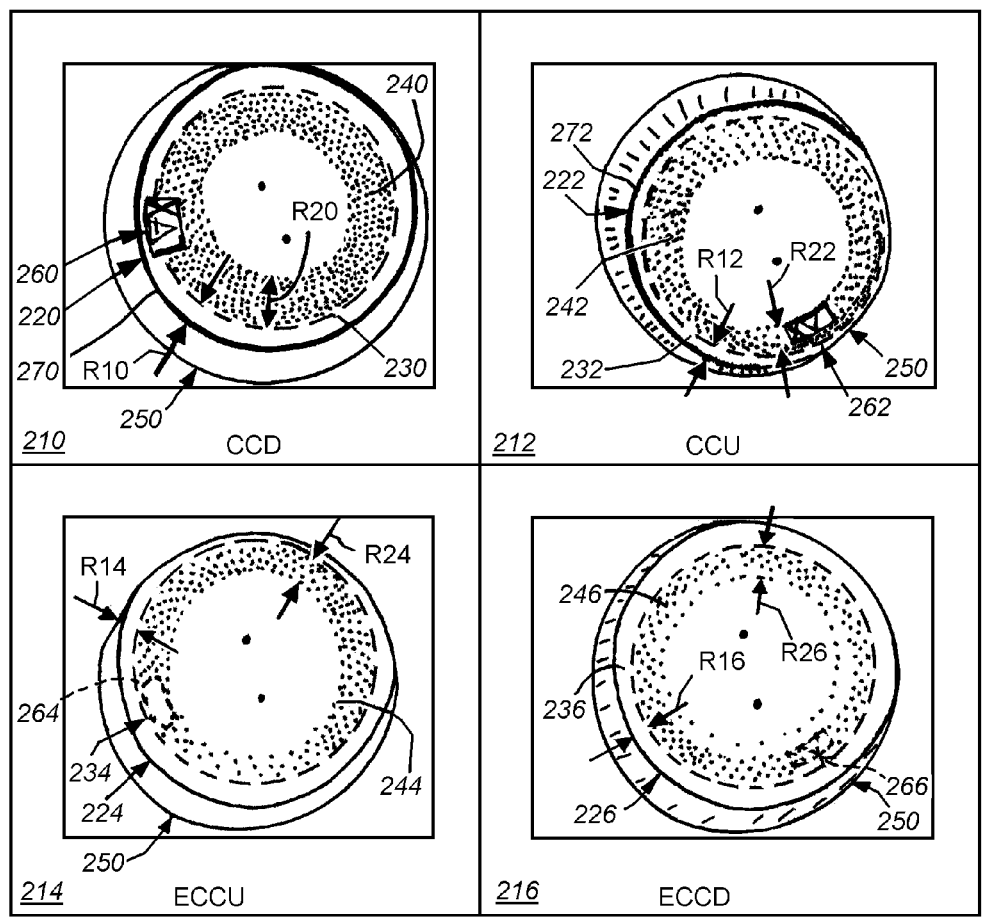
FIG. 2 is a diagram of four images of an exemplary spherical contact lens in the fluid-filled cuvette of FIG. 1, showing four discrete poses for the lens with respect to the bottom of the cuvette.

Reference is now made to FIG. 2, which is a diagram 200 showing four discrete, exemplary images 210, 212, 214 and 216 of a spherical contact lens in accordance with the arrangement of FIG. 1, respectively exhibiting the poses CCD, CCU, ECCU and ECCD. At least a portion of the perimeter of the contact lens in each pose is visible (as the cuvette walls can be inwardly tapered toward its top 122). Each image 210, 212, 214, and 216 includes a respective outer edge 220, 222, 224 and 226 that can be detected by an appropriate vision system tool such as a contrast or edge-detection tool. Notably, each of the contact lens images 210, 212, 214 and 216 also respectively exhibits a lighter-intensity region 230, 232, 234 and 236, respectively, directed radially inward from the outer edge. This lighter-intensity region terminates radially at a contrasting darker-intensity annular region (band) 240, 242, 244 and 246, respectively. The average radius R10, R12, R14 and R16 for the lighter-intensity region (band) for each respective image 210, 212, 214 and 216 can vary for each image and may exhibit a given relative level of brightness. Likewise, the average radius R20, R22, R24 and R26 for the darker-intensity region/band for each respective image 210, 212, 214 and 216 can also vary for each image. Likewise, the overall average intensity of each band can vary. For example, a small dark band 270 and 272 of differing intensity for each image 210, 212 exists just outside the contact lens' perimeter edge. This provides another distinguishing feature. Other geometric variations between the edges of the two or more concentric contrast regions in each image can also occur and the circularity of the outer perimeter edge for everted contact lenses can exhibit a more out-of-round shape than the normal profile.

Thus, there exist a plurality of detectible features that distinguish between each pose for the contact lens. These features, and their relative differences, can allow the illustrative vision system to distinguish between, and classify, each pose.

Note that the cuvette edge 250 is visible in each image. As described below, the cuvette edge 250 can be used as part of the process of identifying and classifying features. The space in the imaged area beyond the cuvette window can be provided in a fixed, opaque shade, such as black. In this manner, the cuvette top and bottom exclusively transmit light upon which contrast differences can be determined by the vision system.

The contact lens images 210, 212, 214 and 216 also reveal an exemplary etched or printed mark 260, 262, 264 (not readily visible) and 266, respectively located in the vicinity of the perimeter edge of the subject contact lens (where it does not interfere with normal vision through the pupil of the wearer's eye). The mark is typically provided on the outer surface of the contact lens, but can be embedded in the material or placed on an inside (eye-contacting surface of the lens). Each image 210, 212, 214 and 216 respectively shows the mark in a different orientation (i.e. rotated and in either a forward or reversed (e.g. mirror image) orientation. As described further below, the radial focus gradient for each mark can differ for each respective pose. This provides further information to the vision system on the orientation of the subject contact lens in the acquired image. Note that when a mark is present on a contact lens, the mark can be any character(s) and/or pictorial graphic(s) that is/are non-transparent to the illumination light, and can be effectively resolved by a camera and analyzed by a vision system.

Figure 3:
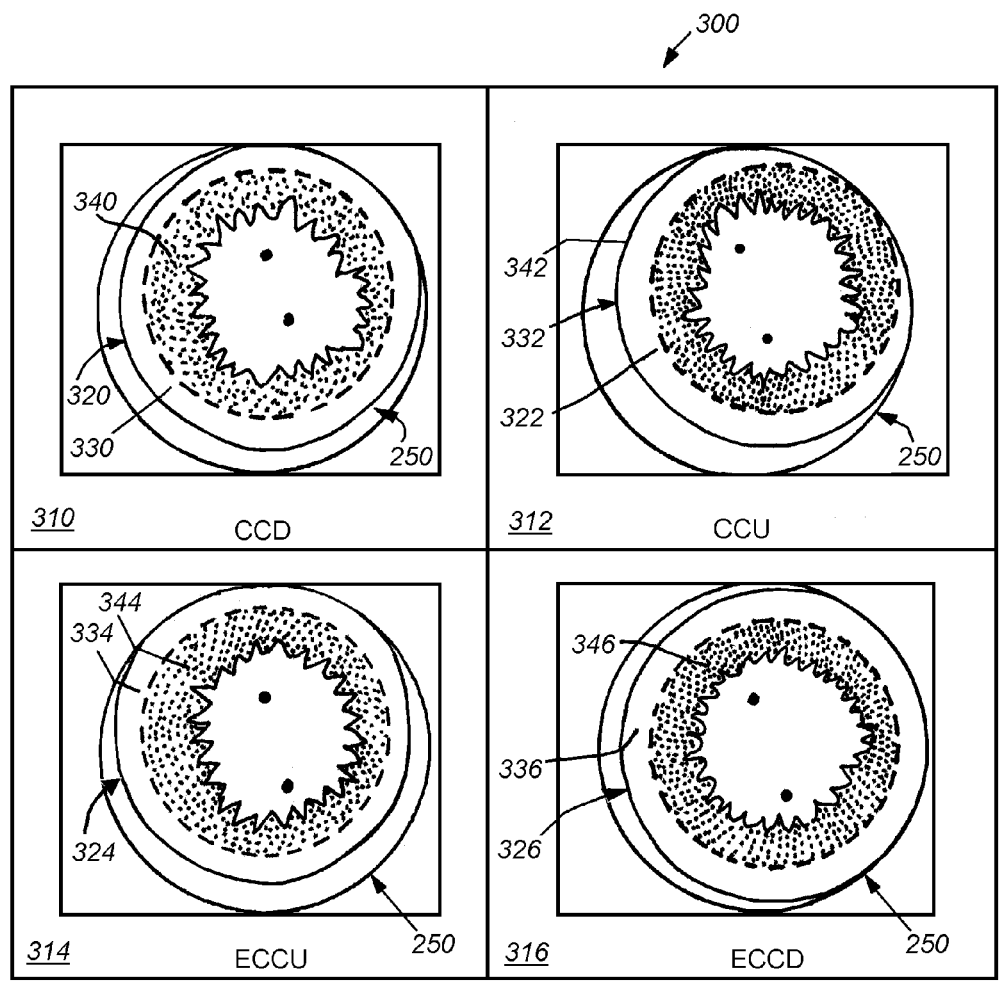
FIG. 3 is a diagram of four images of an exemplary spherical contact lens having a printed iris pattern in the fluid-filled cuvette of FIG. 1, showing four discrete poses for the lens with respect to the bottom of the cuvette.

The variation between features can be used to identify and classify pose in other types of contact lenses. As shown in the diagram 300 of FIG. 3, four discrete images 310, 312, 314 and 316 represent four respective poses CCD, CCU, ECCU and ECCD for a contact lens having an exemplary color-printed iris (i.e. an eye-color changing/enhancing contact lens) pattern 340, 342, 344 and 346, respectively. Each imaged contact lens includes an outer perimeter edge 320, 322, 324 and 326, respectively. Beyond this edge is a region of lighter intensity 330, 332, 334 and 336, respectively. Notably, in each image 310, 312, 314 and 316, the printed iris 340, 342, 344 and 346 provides a large quantity of graphic information that the vision system can use to determine the radial focus gradient and assist in differentiating between contact lens poses. Thus, for the purpose of this description, the term "mark" can be taken broadly to include such printed iris patterns.

The principles described above for differentiating edge features is also applicable to other contact lens types, such as toric contact lenses. Acquired images (not shown) possess similar contrasting edge features that define approximate concentric circles relative to the outer perimeter edge of the contact lens. As described below, the type of lens is specified by the user so that the appropriate set of corresponding training data (i.e. spherical, toric, etc.) is employed by the vision system.

Figure 4:
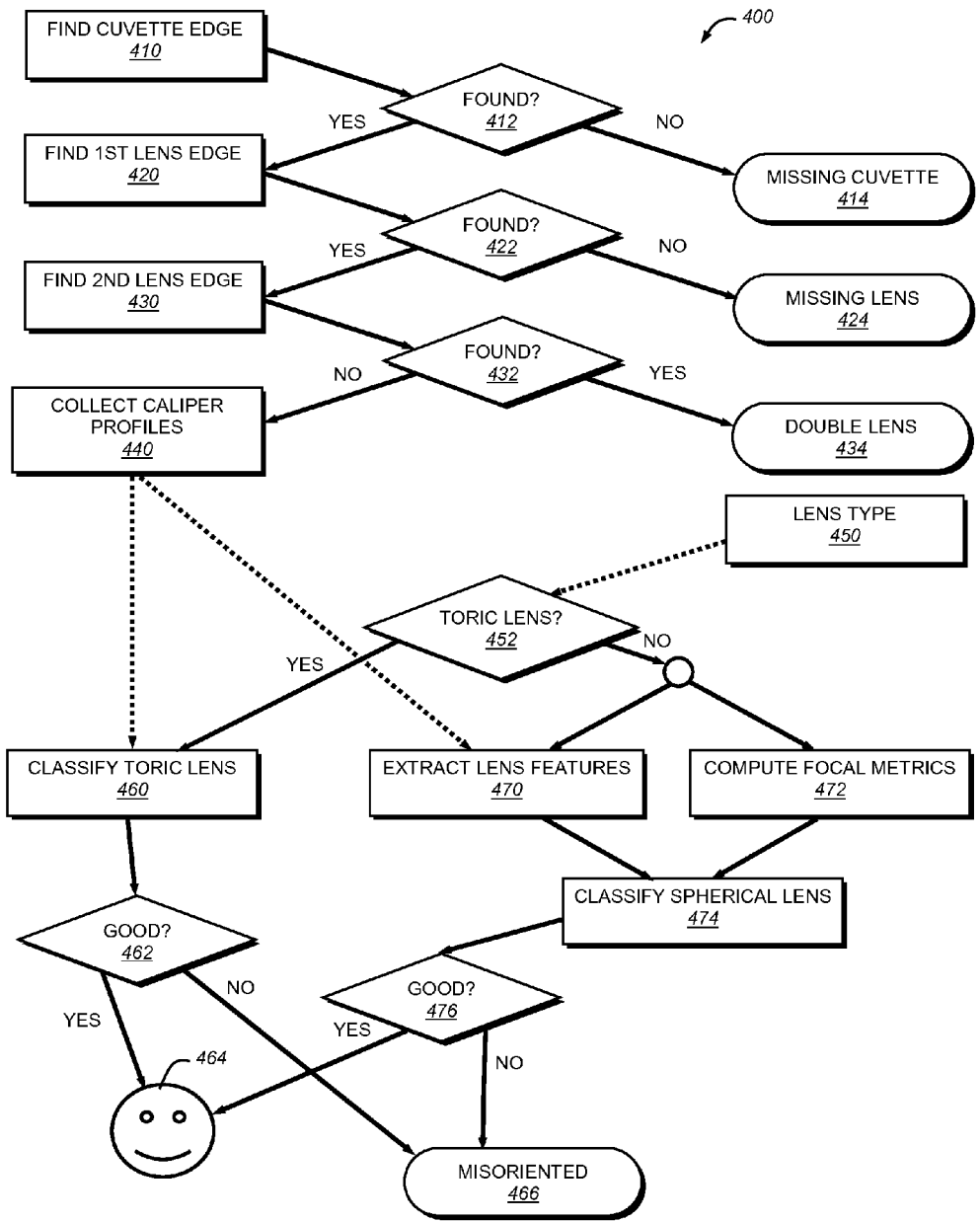
FIG. 4 is a flow diagram of a procedure for identifying and classifying a contact lens in the fluid-filled cuvette of FIG. 1.

An illustrative procedure 400 for identifying contact lens features, and using these features to classify the contact lens pose is shown in further detail in FIG. 4. Briefly, the procedure identifies subtle cues in the image of the contact lens. These cues include focus gradients and dark/bright bands near the edge of the lens. In particular, the procedure 400 processes the image to obtain (a) an average radial intensity profile near the edge of the lens and (b) a focus gradient profile measured in the radial direction from the lens center to its edge. These raw profiles (as well as features computed from these profiles) are used to classify the pose of each lens.

The classifiers used by the procedure are first trained on profile data and features computed from images in a training database of contact lenses with known pose. After training is complete, these same classifiers are then used to classify the pose of each lens that enters the machine. Illustratively, the classifiers can include the well known k-nearest neighbor (KNN) technique, a Bayes classifier and/or a support vector machine (SVM).

The procedure 400 begins with the vision system acquiring an image of the area containing the cuvette. In step 410, the vision system then employs an appropriate tool (e.g. an edge detection tool) to locate the edge of the transparent round window at the bottom of the cuvette, hereinafter referred to as the "cuvette edge". The cuvette should define a predictable feature in terms of size and approximate location. If the edge is not found, then most likely there is no cuvette present (decision step 412 and step 414). This state is indicated and the procedure returns to the beginning awaiting another image acquisition. If the cuvette edge is located (decision step 412), then the procedure finds a first edge of the contact lens (step 420). Finding of this edge feature can also be based on operation of an edge detection tool or similar vision system tool. If the first contact lens edge is not found (decision step 422), then the procedure 400 indicates a missing contact lens (step 424), and returns to await a new image. If the first contact lens edge is found (decision step 422), then the procedure 400 attempts to find a second contact lens edge 430. In general, if two or more lenses are present in the cuvette, their image typically includes at least two crossing points, in the manner of interlocking rings, formed by their edges. If a second (typically crossing) edge is found, then the procedure indicates a double-inclusion of contact lenses in the cuvette (decision step 432 and step 434).

If a single lens is present in the cuvette (decision step 432), then the procedure 400 collects caliper tool profiles from the image (step 400). These profiles are respective plots of image intensity as a function of radial position crossing from the outside to the inside of the contact lens. More generally, the caliper tool includes a function that allows it to generate such one-dimensional intensity profiles from the edge information of each image. Other tools and techniques for obtaining intensity profiles of the contact lens image can be employed in alternate embodiments that should be clear to those of skill in the art. The procedure 400 receives an input of lens type (450), typically from a user interface or a programmable logic controller (PLC). In an embodiment, the lens is either spherical or toric. If the lens is toric, then decision step 452 branches to the classification process for a toric lens (step 460). The caliper tool's radial intensity profiles from step 440 are used in the classification process (460). The classification process uses classifiers, as described above, which operate with respect to the caliper profiles to compare these to candidate intensity profiles for training images in each of the four poses. This process can be accomplished using known techniques. In the case of a toric lens the geometry offers sufficient caliper profile detail to classify the lens. Based upon that classification, the pose of the contact lens is determined (i.e. CCD, CCU, ECCU and ECCD). If the result is good (CCD), then decision step 462 indicates a good pose to the user/system, and passes the contact lens on to other processes. If the decision step 462 determines that the pose from classification (460) is unacceptable (bad—CCU, ECCU or ECCD), then the system is notified that the contact lens is misoriented (step 466), and appropriate action is taken to correct the presence of a misoriented contact lens—either by flipping the contact lens in the cuvette or discarding it.

If the contact lens type (input 450) is spherical, then the decision step 452 branches to a process for classifying spherical lenses (either with or without printed iris). This process performs two concurrent steps of feature extraction of the contact lens, including extraction of the features from the radial caliper profiles in step 470, and extraction of features from the image focus metrics in step 472.

Illustratively, the features extracted from the radial intensity caliper profiles in step 470 include (a) intensity of a dark band just outside the edge of the lens (e.g. 270 in FIG. 2), (b) intensity of a light band inside the lens (e.g. 230), and (c) blurriness of the lens edge. The features extracted from the image focus metrics in step 472 include average slope and slope error. Step 472 includes edge detection enhanced by specific morphological filters. The image is then divided into concentric rings, and the average sharpness is computed for each of the rings. A linear regression algorithm is applied to the resulting radial data to obtain the two features: the regression slope and the regression error. The set of features extracted in steps 470 and 472 is then used both to train the classifier 474 during the training phase and determining the pose of the lens during runtime operations.

Note that, as described generally above, focus metrics step 472 include providing a radial focus profile based upon the mark features (graphic or character mark, printed iris, etc.). Illustratively, this focus profile can be provided and processed in a procedurally similar manner as the radial intensity profile. In general, the radial focus profile will exhibit a high amplitude if the focus is good and a low amplitude if the focus is poor. For example, if the contact lens is in a good, CCU orientation, then the printed iris (FIG. 3) will become more blurred radially outwardly from the center region of the contact lens. This is because the center of a CCU lens is resting on the surface of best camera focus (the bottom of the cuvette) whereas the outer edge of the lens is maximally elevated away from the surface of best camera focus. Illustratively, on non-printed spherical lenses (FIG. 2), the radial focus metric relates to the contrast in the mark (e.g. 260), providing an indication of the relative focus quality at the small versus large radius limits of the mark.

This is used to determine the pose. If the decision step 476 determines that the pose is good (CCD), then the procedure 400 indicates a proper pose (step 464). If the decision step 476 determines that the pose is "bad" (or otherwise unacceptable) unacceptable (CCU, ECCU or ECCD), then the system indicates a misoriented (step 466) requiring appropriate action.

In an illustrative embodiment, training data for use in the procedure 400 can be generated by running the edge detection tool, caliper tool and other processes (e.g. focal metric determination) on a large number of acquired images of one or more contact lenses of each type in each of the four poses. This iterative process thereby creates a database of information for each pose.

It should be clear that the system and method for determining contact lens orientation/pose in a contact lens test arrangement effectively and efficiently provides accurate pose information based upon a face-on view of the contact lens within an enclosed structure, such as a cuvette, where side view information is generally unavailable. This system and method can employ conventional vision system tools and classifiers with appropriate training data.

The foregoing has been a detailed description of illustrative embodiments of the invention. Various modifications and additions can be made without departing from the spirit and scope of this invention. Each of the various embodiments described above may be combined with other described embodiments in order to provide multiple features. Furthermore, while the foregoing describes a number of separate embodiments of the apparatus and method of the present invention, what has been described herein is merely illustrative of the application of the principles of the present invention. For example, the position of the camera and illuminator can be reversed with respect to the top and bottom of the cuvette. Likewise, multiple illuminators can be employed or the illuminator(s) and/or camera can be mounted at a non-aligned position, and at a non-parallel angle with respect to the cuvette's longitudinal axis. For example an off-axis illumination configuration can be provided. Moreover, the illuminator(s) and the camera can be positioned all on the same side of the cuvette, or in addition to an illuminator on the opposite side of the cuvette. Furthermore, the various vision tools and processes used to identify features and characterize the contact lens pose are illustrative of a wide variety of tools/combinations of tools that can be used to perform the general functions of the system and method described herein. Other equivalent tools and processes can be substituted in accordance with ordinary skill. Accordingly, this description is meant to be taken only by way of example, and not to otherwise limit the scope of this invention.

What is claimed is:

1. A system for determining orientation of a contact lens residing on a bottom of a cuvette comprising:
    a vision system camera oriented with a lens axis approximately aligned with a longitudinal axis of the cuvette, constructed and arranged to acquire an image of the contact lens;
    an edge detection vision tool that locates the contact lens in the image and that determines edges within the image; and
    a classifier vision tool that, based upon at least one of locations of the edges and features within the image classifies a concave and everted orientation of the contact lens relative to training information with respect to each of a plurality of predetermined contact lens orientations.

2. The system as set forth in claim 1 wherein the classifier is constructed and arranged to classify based upon at least one of (a) radial gradient information relative to bands of light and dark intensity adjacent to an outer edge of the contact lens in the image and (b) focus gradient information from a center of the contact lens to the outer edge in the image.

3. The system as set forth in claim 2 further comprising a caliper tool that provides radial intensity profiles and wherein the focus gradient information is based upon a radial focus gradient with respect to a mark or a printed iris.

4. The system as set forth in claim 2 wherein the contact lens is a toric lens.

5. The system as set forth in claim 3 further comprising a feature extractor vision tool that extracts the features within the image for use by the classifier.

6. The system as set forth in claim 5 wherein the contact lens is a spherical contact lens.

7. The system as set forth in claim 2 wherein the radial gradient information comprises an average radial intensity profile adjacent to the edge of the lens in the image.

8. The system as set forth in claim 1 wherein the cuvette bottom is at least in part transparent, and the cuvette defines a light-transmissive top and sidewalls that are at least one of opaque and optically diffuse.

9. The system as set forth in claim 8 wherein the vision system camera is oriented to image the contact lens through the transparent bottom and further comprising an illuminator located to illuminate the contact lens through the light-transmissive top.

10. A method for determining orientation of a contact lens residing on a bottom of a cuvette comprising the steps of:
    acquiring, with a vision system camera oriented with a lens axis approximately aligned with a longitudinal axis of the cuvette, an image of the contact lens;
    locating the contact lens in the image and that determining edges within the image; and
    based upon at least one of locations of the edges and features within the image classifying a concave and evert orientation of the contact lens relative to training information with respect to each of a plurality of predetermined contact lens orientations.

11. The method as set forth in claim 10 wherein the step of classifying is based upon at least one of (a) radial intensity gradient information relative to bands of light and dark intensity adjacent to an outer edge of the contact lens in the image and (b) focus gradient information from a center of the contact lens to the outer edge in the image based upon a mark or a printed iris.

12. The method as set forth in claim 11 wherein the radial intensity gradient information includes radial intensity profiles based upon a caliper tool.

13. The method as set forth in claim 11 wherein the contact lens is a toric lens.

14. The method as set forth in claim 12 further comprising extracting the features within the image for use by the step of classifying.

15. The method as set forth in claim 14 wherein the contact lens is a spherical contact lens.

16. The method as set forth in claim 11 wherein the radial gradient information comprises an average radial intensity profile adjacent to the edge of the lens in the image.

17. The method as set forth in claim 10 wherein the cuvette bottom is at least in part transparent, and the cuvette defines a light-transmissive top and sidewalls that are at least one of opaque and optically diffuse.

18. The method as set forth in claim 17 further comprising orienting vision system camera to image the contact lens through the transparent bottom and locating an illuminator to illuminate the contact lens through the light-transmissive top.

\* \* \* \* \*